(12) United States Patent
Hendrix et al.

(10) Patent No.: US 7,256,288 B2
(45) Date of Patent: Aug. 14, 2007

(54) HETEROARYL CARBOXYLIC ACID AMIDES

(75) Inventors: Martin Hendrix, Odenthal (DE); Frank-Gerhard Böss, Berkshire (GB); Christina Erb, Kriftel (DE); Joachim Krüger, Düsseldorf (DE); Joachim Luithle, Wülfrath (DE); Christoph Methfessel, Wuppertal (DE); Rudy Schreiber, Menlo Park, CA (US); Welf-Burkhard Wiese, Wermelskirchen (DE)

(73) Assignee: Bayer HealthCare AG, Leverkusen (DE)

( * ) Notice: Subject to any disclaimer, the term of this patent is extended or adjusted under 35 U.S.C. 154(b) by 0 days.

(21) Appl. No.: 10/496,404

(22) PCT Filed: Nov. 6, 2002

(86) PCT No.: PCT/EP02/12375

§ 371 (c)(1),
(2), (4) Date: May 6, 2005

(87) PCT Pub. No.: WO03/043991

PCT Pub. Date: May 30, 2003

(65) Prior Publication Data

US 2005/0209236 A1    Sep. 22, 2005

(30) Foreign Application Priority Data

Nov. 19, 2001 (DE) ................ 101 56 719

(51) Int. Cl.
*C07D 239/02* (2006.01)
*C07D 453/02* (2006.01)

(52) U.S. Cl. .............. 544/297; 546/133; 514/272; 514/305

(58) Field of Classification Search ......... 514/272, 514/305; 544/297; 546/133
See application file for complete search history.

(56) References Cited

U.S. PATENT DOCUMENTS 5,206,246 A * 4/1993 Langlois et al. ............ 514/272

FOREIGN PATENT DOCUMENTS

| DE | 3724059 | 2/1988 |
| EP | 0327335 | 8/1989 |
| WO | 8501048 | 3/1985 |
| WO | 9117161 | 11/1991 |
| WO | 0160821 | 8/2001 |

* cited by examiner

*Primary Examiner*—D. Margaret Seaman

(57) ABSTRACT

The invention relates to novel heteroaryl carboxamides, a process for their preparation, and pharmaceutical compositions containing them. These materials are useful for the treatment and/or prophylaxis of diseases and for improving perception, concentration, learning and/or memory.

5 Claims, No Drawings

HETEROARYL CARBOXYLIC ACID AMIDES

This application is a 371 of PCT/EP02/12375 filed Nov. 6, 2002 which claims priority to Germany 101 56 719.7, filed Nov. 19, 2001.

The invention relates to novel heteroaryl carboxamides, processes for their preparation, and their use for producing medicaments for the treatment and/or prophylaxis of diseases and for improving perception, concentration, learning and/or memory.

Nicotinic acetylcholine receptors (nAChR) form a large family of ion channels which are activated by the messenger acetylcholine which is produced in the body (Galzi and Changeux, *Neuropharmacol.* 1995, 34, 563-582). A functional nAChR consists of five subunits which may be different (certain combinations of α1-9 and β1-4, γ, δ, ε subunits) or identical (α7-9). This leads to the formation of a diversity of subtypes which differ in the distribution in the muscles, the nervous system and other organs (McGehee and Role, *Annu. Rev. Physiol.* 1995, 57, 521-546). Activation of nAChR leads to influx of cations into the cell and to stimulation of nerve cells or muscle cells. Selective activation of individual nAChR subtypes restricts this stimulation to the cell types which have the corresponding subtype and is thus able to avoid unwanted side effects such as, for example, stimulation of nAChR in the muscles. Clinical experiments with nicotine and experiments in various animal models indicate that central nicotinic acetylcholine receptors are involved in learning and memory processes (e.g. Rezvani and Levin, *Biol. Psychiatry* 2001, 49, 258-267). Nicotinic acetylcholine receptors of the alpha7 subtype (α7 nAChR) have a particularly high concentration in regions of the brain which are important for learning and memory, such as the hippocampus and the cerebral cortex (Séguéla et al., *J. Neurosci.* 1993, 13, 596-604). The α7 nAChR has a particularly high permeability for calcium ions, increases glutamatergic neurotransmission, influences the growth of axons and, in this way, modulates neuronal plasticity (Broide and Leslie, *Mol. Neurobiol.* 1999, 20, 1-16).

WO 85/01048 and DE-A-3724059 describe certain heteroaryl carboxamides as serotonin M or $5HT_3$ antagonists for the treatment of arrhythmias and pain, and psychoses and disorders of consciousness.

EP-A-0 327 335 discloses certain heteroaryl carboxamides with a memory-improving effect.

Isoquinolinecarboxamides with an $5HT_3$-antagonistic effect are disclosed in WO 91/17161 for the treatment of CNS disorders.

WO 01/60821 discloses biaryl carboxamides with affinity for the α7 nAChR for the treatment of disorders of learning and perception.

Certain 2- and 3-quinolinecarboxamides are described in Orjales et al. *Drug Des. Discovery* 2000, 16, 271-279 as ligands on the $5HT_3$ receptor.

The present invention relates to compounds of the general formula (I)

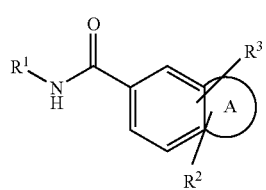

(I)

in which $R^1$ is an azabicyclo[m.n.o]alkyl radical having 7 to 11 ring atoms, in which m, n and o are identical or different and are 0, 1, 2 or 3, and where the radical is optionally substituted by $(C_1-C_6)$-alkyl, the ring A is pyrimido, or is optionally benzo-fused pyrido, pyridazo or pyridazino, and $R^2$ and $R^3$ are identical or different and are radicals selected from the group of hydrogen, halogen, formyl, carbamoyl, cyano, trifluoromethyl, trifluoromethoxy, nitro, $(C_1-C_6)$-alkyl, $(C_1-C_6)$-alkoxy, $(C_1-C_6)$-alkylthio, $(C_3-C_8)$-cycloalkyl, 4- to 8-membered heterocyclyl, phenyl or 5- to 6-membered heteroaryl, where phenyl and heteroaryl are optionally substituted by halogen, $(C_1-C_4)$-alkyl, $(C_1-C_4)$-alkoxy, amino, mono- or di-$(C_1-C_4)$-alkylamino, $(C_1-C_4)$-alkanoylamino or $(C_1-C_4)$-alkanesulfonylamino.

The radicals $R^2$ and $R^3$ in the general formula (I) may be bonded independently of one another to ring A or to the benzene ring. The radicals $R^2$ and $R^3$ are preferably bonded to ring A.

The compounds of the invention may exist in stereoisomeric forms which either are related as image and mirror image (enantiomers) or which are not related as image and mirror image (diastereomers). The invention relates both to the enantiomers or diastereomers or to respective mixtures thereof. These mixtures of enantiomers and diastereomers can be separated in a known manner into the stereoisomerically pure constituents.

The compounds of the invention may also exist in the form of their salts, hydrates and/or solvates.

Salts which are preferred for the purposes of the invention are physiologically acceptable salts of the compounds of the invention.

Physiologically acceptable salts of the compounds of the invention may be acid addition salts of the compounds with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

However, salts which may be mentioned are also salts with conventional bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabiethylamine, 1-ephenamine or methylpiperidine.

Hydrates of the compounds of the invention are stoichiometric compositions of the compounds or its salts with water.

Solvates of the compounds of the invention are stoichiometric compositions of the compounds or its salts with solvent.

For the purposes of the present invention, the substituents generally have the following meaning:

$(C_1-C_4)$-Alkanoylamino is a straight-chain or branched alkanoylamino radical having 1 to 4 carbon atoms. A straight-chain or branched alkanoylamino radical having 1 to 3 carbon atoms is preferred. Preferred examples which may be mentioned are: formylamino, acetylamino, propanoylamino, n-butanoylamino, i-butanoylamino.

$(C_1-C_6)$- and $(C_1-C_4)$-alkoxy are a straight-chain or branched alkoxy radical having, respectively, 1 to 6 and 1 to 4 carbon atoms. Preference is given to a straight-chain or branched alky radical having 1 to 4, particularly preferably having 1 to 3, carbon atoms. Preferred examples which may be mentioned are: methoxy, ethoxy, n-propoxy, iso-propoxy, tert-butoxy, n-pentoxy and n-hexoxy.

($C_1$-$C_6$)- and ($C_1$-$C_4$)-alkyl are a straight-chain or branched alkyl radical having, respectively, 1 to 6 and 1 to 4 carbon atoms. Preference is given to a straight-chain or branched alkyl radical having 1 to 4, particularly preferably having 1 to 3, carbon atoms. Preferred examples which may be mentioned are: methyl, ethyl, n-propyl, isopropyl, tert-butyl, n-pentyl and n-hexyl.

Mono-($C_1$-$C_4$)-alkylamino is a straight-chain or branched alkylamino radical having 1 to 4 carbon atoms. A straight-chain or branched alkylamino radical having 1 to 3 carbon atoms is preferred. Preferred examples which may be mentioned are: methylamino, ethylamino, n-propylamino, isopropylamino, tert-butylamino.

Di-($C_1$-$C_4$)-alkylamino is a straight-chain or branched dialkylamino radical, where the alkyl radicals may be identical or different and each contain 1 to 4 carbon atoms. A straight-chain or branched dialkylamino radical where the alkyl radical in each case contains 1 to 3 carbon atoms is preferred. Preferred examples which may be mentioned are: dimethylamino, diethylamino, di-n-propylamino, diisopropylamino, di-t-butylamino, di-n-pentylamino, di-n-hexylamino, ethylmethylamino, isopropylmethylamino, n-butylethylamino.

($C_1$-$C_4$)-Alkanesulfonylamino are a straight-chain or branched alkanesulfonylamino radical having 1 to 4 carbon atoms. A straight-chain or branched alkanesulfonylamino radical having 1 to 3 carbon atoms is preferred. Preferred examples which may be mentioned are: methanesulfonylamino, ethanesulfonylamino, n-propanesulfonylamino, isopropanesulfonylamino, tert-butanesulfonylamino.

($C_1$-$C_6$)-Alkylthio is a straight-chain or branched alkylthio radical having 1 to 6 carbon atoms. Preference is given to a straight-chain or branched alkylthio radical having 1 to 4, particularly preferably having 1 to 3, carbon atoms. Preferred examples which may be mentioned are: methylthio, ethylthio, n-propylthio, isopropylthio, tert-butylthio, n-pentylthio and n-hexylthio.

The azabicyclo[m.n.o]alkyl radical having 7 to 11 ring atoms is preferably bonded via a carbon ring atom to the adjacent amide nitrogen atom. The nitrogen ring atom and the amide nitrogen atom are preferably not located on the same carbon ring atom. Azabicyclo[m.n.o]alkyl radicals in which the nitrogen ring atom and the amide nitrogen atom are separated by two carbon ring atoms are particularly preferred. Examples of azabicyclo[m.n.o]alkyl radicals which may be mentioned are: 8-azabicyclo[3.2.1]octyl (tropane), 1-azabicyclo[3.2.1]octyl (isotropane), 8-azabicyclo[3.3.1]nonyl (granatane), 1-azabicyclo[3.3.1]nonyl (isogranatane), 1-azabicyclo[2.2.2]octyl (quinuclidine), 2-azabicyclo[2.2.2]octyl (isoquinuclidine).

($C_3$-$C_8$)-Cycloalkyl is cyclopropyl, cyclopentyl, cyclobutyl, cyclohexyl, cycloheptyl or cyclooctyl. Those which may be mentioned as preferred are: cyclopropyl, cyclopentyl and cyclohexyl.

Halogen is fluorine, chlorine, bromine and iodine. Fluorine, chlorine and bromine are preferred. Fluorine and chlorine are particularly preferred.

5- to 6-membered heteroaryl is an aromatic radical having 5 to 6 ring atoms and up to 4 heteroatoms from the series S, O and/or N. The heteroaryl radical may be bonded via a carbon atom or heteroatom. Preferred examples which may be mentioned are: thienyl, furyl, pyrrolyl, thiazolyl, oxazolyl, imidazolyl, tetrazolyl, pyridyl, pyrimidinyl, and pyridazinyl.

4- to 8-membered heterocyclyl is a mono- or polycyclic, heterocyclic radical having 4 to 8 ring atoms and up to 3, preferably 1, heteroatoms or hetero groups from the series N, O, S, SO, $SO_2$. Mono- or bicyclic heterocyclyl is preferred. Monocyclic carbocyclyl is particularly preferred. N and O are preferred heteroatoms. The heterocyclyl radicals may be saturated or partially unsaturated. Saturated heterocyclyl radicals are preferred. The heterocyclyl radicals may be bonded via a carbon atom or a heteroatom. 5- to 7-membered monocyclic saturated heterocyclyl radicals having up to two heteroatoms from the series O, N and S are particularly preferred. Preferred examples which may be mentioned are: oxetan-3-yl, pyrrolidin-2-yl, pyrrolidin-3-yl, pyrrolinyl, tetrahydrofuranyl, tetrahydrothienyl, pyranyl, piperidinyl, thiopyranyl, morpholinyl, perhydroazepinyl.

If radicals in the compounds of the invention are optionally substituted, the radicals may, unless specified otherwise, have one or more identical or different substituents. Substitution by up to three identical or different substituents is preferred.

Preferred compounds of the general formula (I) are those in which $R^1$ is an azabicyclo[m.n.o]alkyl radical having 7, to 9 ring atoms, in which m, n and o are identical or different and are 0, 1, 2 or 3, and where the radical is optionally substituted by methyl or ethyl, and the ring A, $R^2$ and $R^3$ have the meaning indicated above.

Particularly preferred compounds of the general formula (I) are those in which $R^1$ is 1-azabicyclo[2.2.2]oct-3-yl, and the ring A, $R^2$ and $R^3$ have the meaning indicated above.

Likewise preferred compounds of the general formula (I) are those in which the ring A is pyrido, and $R^1$, $R^2$ and $R^3$ have the meaning indicated above.

Particularly preferred compounds of the general formula (I) are those in which the ring A together with the fused-on benzene residue is quinolin-6-yl, and $R^1$, $R^2$ and $R^3$ have the meaning indicated above.

Likewise preferred compounds of the general formula (I) are those in which $R^2$ and $R^3$ are identical or different and are radicals selected from the group of hydrogen, halogen, cyano, trifluoromethyl, methyl and ethyl, and the ring A and $R^1$ have the meaning indicated above.

Particularly preferred compounds of the general formula (I) are those in which $R^2$ and $R^3$ are identical or different and are radicals selected from the group of hydrogen, halogen and methyl, and the ring A and $R^1$ have the meaning indicated above.

Combinations of two or more of the abovementioned preferred ranges are very particularly preferred.

Likewise very particularly preferred are compounds of the general formula (I)
in which
$R^1$ is 1-azabicyclo[2.2.2]oct-3-yl, the ring A together with the fused-on benzene residue is quinolin-5-yl or quinolin-6-yl, and $R^2$ and $R^3$ are identical or different and are radicals selected from the group of hydrogen, fluoro, chloro, and methyl.

The invention further relates to processes for preparing the compounds of the formula (I), characterized in that compounds of the general formula (II)

   (II)

in which $R^1$ has the abovementioned meaning, are reacted with a compound of the general formula (III)

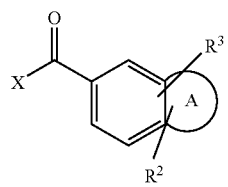   (III)

in which the ring A, $R^2$ and $R^3$ have the abovementioned meaning, and

X is hydroxyl or a suitable leaving group, in an inert solvent, where appropriate in the presence of a condensing agent, and where appropriate in the presence of a base.

If X is a leaving group, chloro, mesyloxy and isobutyloxycarbonyloxy, especially chloro, are preferred.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, ethyl acetate, acetone, dimethylformamide, dimethylacetamide, 1,2-dimethoxyethane, dimethyl sulfoxide, acetonitrile or pyridine, with preference for tetrahydrofuran, dimethylformamide or chloroform.

Condensing agents are, for example, carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide) or carbonyl compounds such as carbonyldiimidazole, or 1,2-oxazolium compounds such as 2-ethyl-5-phenyl-1,2-oxazolium-3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU) or benzotriazol-1-yloxytris(dimethylamino)phosphonium hexafluorophosphate (BOP), or mixtures thereof.

It may be advantageous where appropriate to use these condensing agents in the presence of an auxiliary nucleophile such as, for example, 1-hydroxybenzotriazole (HOBt).

Examples of bases are alkali metal carbonates such as, for example, sodium or potassium carbonate or bicarbonate, or organic bases such as trialkylamines, e.g. triethylamine, or N-methylmorpholine, N-methylpiperidine, 4-dimethylaminopyridine or diisopropylethylamine.

Particular preference is given to the combination of N-(3-dimethylaminoisopropyl)-N'-ethylcarbodiimide hydrochloride (EDC) and 1-hydroxybenzotriazole (HOBt) in dimethylformamide.

The process of the invention is preferably carried out in a temperature range from room temperature to 50° C. under atmospheric pressure.

The compounds of the general formulae (II) and (III) are known or can be synthesized by known processes from the appropriate precursors (cf., for example, "Comprehensive Heterocyclic Chemistry", Katritzki et al., editors; Elsevier, 1996).

Thus, for example, quinolinecarboxylic acids [$X^1$ is hydroxyl and the ring A is [b]pyrido in compounds of the general formula (III)] can be obtained by oxidizing the corresponding methylquinolines (Miller et al. *Chem. Ber.* 1890, 23, 2263 ff.) or the corresponding aldehydes (Howitz et al. *Justus Liebigs Ann. Chem.* 1913, 396, 37) with suitable oxidizing agents such as, for example, $Cr_2O_3$.

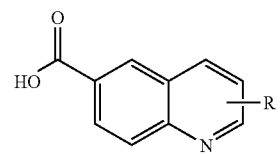

A further possibility is, for example, to obtain 6-quinolinecarboxylic acids by reacting 4-aminobenzoic acid with suitable enones (John et al. *J. Prakt. Chem.* 1925, 111, 95), as illustrated by way of example by the following synthetic scheme.

Synthetic scheme 1:

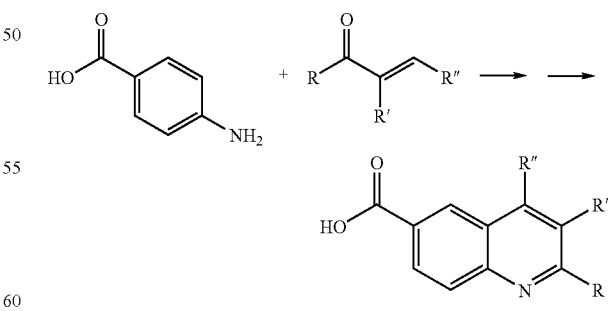

An alternative possibility is to prepare quinolinecarboxamides of the invention by reacting the corresponding iodine- and amino-substituted benzamides in the presence of suitable catalysts with allyl alcohols and propargyl alcohols (cf. Kuo et al. *Tetrahedron Lett.* 1991, 32, 569), as illustrated by way of example by the following synthetic scheme.

Synthetic scheme 2:

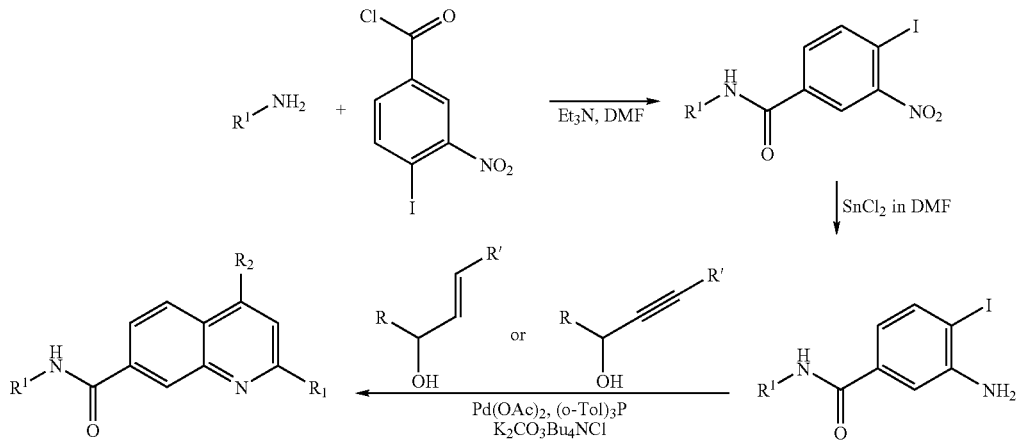

The compounds of the invention of the general formula (I) are suitable for use as medicaments for the treatment and/or prophylaxis of diseases in humans and/or animals.

The compounds of the invention show a valuable range of pharmacological effects which could not have been predicted.

They are notable as ligands, especially agonists, at the α7 nAChR.

The compounds of the invention can, because of their pharmacological properties, be employed alone or in combination with other active ingredients for the treatment and/or prevention of cognitive impairments, especially of Alzheimer's disease. Because of their selective effect as α7 nAChR agonists, the compounds of the invention are particularly suitable for improving perception, concentration, learning or memory, especially after cognitive impairments like those occurring for example in situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic craniocerebral trauma, general concentration impairments, concentration impairments in children with learning and memory problems, attention deficit hyperactivity disorder, Alzheimer's disease, vascular dementia, Lewy body dementia, dementia with degeneration of the frontal lobes, including Pick's syndrome, Parkinson's disease, progressive nuclear palsy, dementia with corticobasal degeneration, amyotrophic lateral sclerosis (ALS), Huntington's disease, multiple sclerosis, thalamic degeneration, Creutzfeld-Jacob dementia, HIV dementia, schizophrenia, schizophrenia with dementia or Korsakoff's psychosis.

The compounds of the invention can be employed alone or in combination with other medicaments for the prophylaxis and treatment of acute and/or chronic pain (for a classification, see "Classification of Chronic Pain, Descriptions of Chronic Pain Syndromes and Definitions of Pain Terms", 2nd edition, Meskey and Begduk, editors; IASP Press, Seattle, 1994), especially for the treatment of cancer-induced pain and chronic neuropathic pain like, for example, that associated with diabetic neuropathy, postherpetic neuralgia, peripheral nerve damage, central pain (for example as a consequence of cerebral ischemia) and trigeminal neuralgia, and other chronic pain such as, for example, lumbago, backache (low back pain) or rheumatic pain. In addition, these substances are also suitable for the therapy of primary acute pain of any origin and of secondary states of pain resulting therefrom, and for the therapy of states of pain which were formerly acute and have become chronic.

The in vitro effect of the compounds of the invention can be shown in the following assays:

1. Determination of the Affinity of Test Substances for α7 nAChR by Inhibition of [$^3$H]-methyllycaconitine Binding to Rat Brain Membranes The [$^3$H]-methyllycaconitine binding assay is a modification of the method described by Davies et al. (*Neuropharmacol.* 1999, 38, 679-690).

Rat brain tissue (hippocampus or whole brain) is homogenized in homogenization buffer (10% w/v) (0.32 M sucrose, 1 mM EDTA, 0.1 mM phenylmethylsulfonyl fluoride (PMSF), 0.01% (w/v) NaN$_3$, pH 7.4, 4° C.) at 600 rpm in a glass homogenizer. The homogenate is centrifuged (1000×g, 4° C., 10 min) and the supernatant is removed. The pellet is resuspended (20% w/v) and the suspension is centrifuged (1000×g, 4° C., 10 min). The two supernatants are combined and centrifuged (15 000×g, 4° C., 30 min). This pellet is referred to as the P2 fraction.

The P2 pellet is twice washed with binding buffer (50 mM Tris-HCl, 1 mM MgCl$_2$, 120 mM NaCl, 5 mM KCl, 2 mM CaCl$_2$, pH 7.4) and centrifuged (15 000×g, 4° C., 30 min).

The P2 membranes are resuspended in binding buffer and incubated in a volume of 250 μl (amount of membrane protein 0.1-0.5 mg) in the presence of 1-5 nM [$^3$H]-methyllycaconitine, 0.1% (w/v) BSA (bovine serum albumin) and various concentrations of the test substance at 21° C. for 2.5 h. Nonspecific binding is determined by incubation in the presence of 1 μM α-bungarotoxin or 100 μM nicotine or 10 μM MLA (methyllycaconitine).

The incubation is stopped by adding 4 ml PBS (20 mM Na$_2$HPO$_4$, 5 mM KH$_2$PO$_4$, 150 mM NaCl, pH 7.4, 4° C.) and filtering through type A/E glass fibre filters (Gelman Sciences) which have previously been placed in 0.3% (v/v) polyethyleneimine (PEI) for 3 h. The filters are washed twice with 4 ml of PBS (4° C.), and the bound radioactivity is determined by scintillation measurement. All the assays are carried out in triplicate. The dissociation constant K$_i$ of the test substance was determined from the IC$_{50}$ of the compounds (concentration of the test substance at which 50% of the ligand bound to the receptor is displaced), the dissociation constant $K_D$ and the concentration L of [$^3$H]-methyllycaconitine ($K_i=IC_{50}/(1+L/K_D)$).

In place of [$^3$H]-methyllycaconitine it is also possible to employ other α7 nAChR-selective radioligands such as, for example, [$^{125}$I]-α-bungarotoxin or nonselective nAChR radioligands together with inhibitors of other nAChRs.

The suitability of the compounds of the invention for the treatment of cognitive impairments can be shown in the following animal models:

2. Object Recognition Test

The object recognition test is a memory test. It measures the ability of rats (and mice) to distinguish between familiar and unfamiliar objects.

The test is carried out as described (Blokland et al., NeuroReport 1998, 9, 4205-4208; Ennaceur, A., Delacour, J., Behav. Brain Res. 1988, 31, 47-59; Ennaceur, A., Meliani, K., Psychopharmacology 1992, 109, 321-330; and Prickaerts et al., Eur. J. Pharmacol. 1997, 337, 125-136).

In a first run, a rat is confronted in an otherwise empty observation arena of relatively large size by two identical objects. The rat will investigate, i.e. sniff round and touch, both objects extensively. In a second run, after an interval of 24 hours, the rat is put in the observation arena again. One of the familiar objects has now been replaced by a new, unfamiliar object. If a rat recognizes the familiar object, it will concentrate on investigating the unfamiliar object. However, after 24 hours, a rat has normally forgotten which object it investigated in the first run, and it will therefore inspect both objects to the same extent. Administration of a substance with a learning- and memory-improving effect may lead to a rat recognizing the object seen in the first run 24 hours previously as familiar. It will investigate the new, unfamiliar object in more detail than the familiar one. This memory ability is expressed in a discrimination index. A discrimination index of zero means that the rat investigates both objects, the old and the new, for equal times; that is to say it has not recognized the old object and reacts to both objects as if they were unfamiliar and new. A discrimination index greater than zero means that the rat inspects the new object for longer than the old one; that is to say the rat has recognized the old object.

3. Social Recognition Test:

The social recognition test is a test to examine the learning- or memory-improving effect of test substances.

Adult rats housed in groups are placed singly in test cages 30 minutes before the start of the test. Four minutes before the start of the test, the test animal is put in an observation box. After this adaptation time, a juvenile animal is put in with the test animal and the total time for which the adult animal investigates the juvenile animal is measured for 2 minutes (trial 1). All behaviors clearly directed at the young animal are measured, i.e. anogenital inspection, pursuit and fur care, during which the old animal is no further than 1 cm from the young animal. The juvenile animal is then taken out, and the adult is left in its test cage (for 24-hour retention, the animal is returned to its home cage). The test animal is treated with test substance before or after the first test. Depending on the timing of the treatment, the learning or the storage of the information about the young animal can be influenced by the substance. After a fixed period (retention), the test is repeated (trial 2). A larger difference between the investigation times measured in trials 1 and 2 means that the adult animal has remembered the young animal better.

The compounds of the invention of the general formula (I) are suitable for use as medicaments for humans and animals.

The present invention also includes pharmaceutical preparations which, besides inert, nontoxic, pharmaceutically suitable excipients and carriers, contain one or more compounds of the general formula (I), or which consist of one or more compounds of the general formula (I), and processes for producing these preparations.

The compounds of the formula (I) are to be present in these preparations in a concentration of from 0.1 to 99.5% by weight, preferably from 0.5 to 95% by weight, of the complete mixture.

Besides the compounds of the formula (I), the pharmaceutical preparations may also contain other active pharmaceutical ingredients.

The abovementioned pharmaceutical preparations can be produced by known methods in a conventional way, for example using the excipient(s) or carrier(s).

The novel active ingredients can be converted in a known manner into conventional formulations such as tablets, coated tablets, pills, granules, aerosols, syrups, emulsions, suspensions and solutions, using inert, nontoxic, pharmaceutically suitable carriers or solvents. In these cases, the therapeutically active compound should in each case be present in a concentration of about 0.5 to 90% by weight of the complete mixture, i.e. in amounts which are sufficient to reach the stated dose range.

The formulations are produced for example by extending the active ingredients with solvents and/or carriers, where appropriate with use of emulsifiers and/or dispersants, it being possible, for example when water is used as diluent, where appropriate to use organic solvents as auxiliary solvents.

Administration takes place in a conventional way, preferably orally, transdermally or parenterally, especially perlingually or intravenously. However, it can also take place by inhalation through the mouth or nose, for example with the aid of a spray, or topically via the skin.

It has generally proved advantageous to administer amounts of about 0.001 to 10 mg/kg, on oral administration preferably about 0.005 to 3 mg/kg, of body weight to achieve effective results.

It may, nevertheless, be necessary where appropriate to deviate from the stated amounts, in particular as a function of the body weight or of the mode of administration, of the individual behavior toward the medicament, the nature of its formulation and the time or interval over which administration takes place. Thus, it may be sufficient in some cases to make do with less than the aforementioned minimum amount, whereas in other cases the stated upper limit must be exceeded. Where larger amounts are administered, it may be advisable to divide these into a plurality of single doses over the day.

Abbreviations:

DMF N,N-Dimethylformamide

DMSO Dimethyl sulfoxide

HOBt 1-Hydroxy-1H-benzotriazole×$H_2O$

NMR Nuclear magnetic resonance spectroscopy

RT Room temperature

TBTU O-(Benzotriazol-1-yl)-N,N,N',N'-tetramethyluronium tetrafluoroborate

THF Tetrahydrofuran

Starting Compounds

EXAMPLE 1A

4-Amino-3-iodobenzoic acid

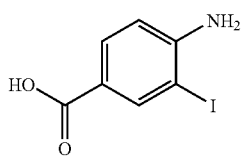

A solution of 3.00 g (10.8 mmol) of methyl 4-amino-3-iodobenzoate and 1.30 g (54.1 mmol) of lithium hydroxide in 150 ml of a dioxane/water mixture (1:1) was stirred at room temperature for 6 h. The dioxane was distilled off in vacuo, and the remaining aqueous phase was adjusted to pH 5 with 1 M hydrochloric acid. The precipitate was filtered off with suction and washed with water. 2.80 g (98%) of the title compound were obtained as a solid.

HPLC (Kromasil RP-18, 60×2.1 mm, eluent=A: $H_2O$+5 mL $HClO_4$/L; B: acetonitrile; gradient=0-4.5 min 98% A—90% B; 4.5-6.5 min 90% B; 0.75 mL/min; temp.: 30° C., UV detection at 210 nm): Rt=3.51 min $^1$H-NMR (300 MHz in $D_6$-DMSO) δ=5.98 (s, 2H), 6.74 (d, 1H), 7.63 (m, 1H), 8.10 (s, 1H), 12.33 (s, broad, 1H)

MS (ESI+): m/z=281 $[M+NH_4]^+$

EXAMPLE 2A

4-Amino-N-(1-azabicyclo[2.2.2]oct-3-yl)-3-iodobenzamide

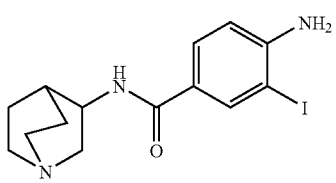

A solution of 2.04 g (10.3 mmol) of 3-aminoquinuclidine dihydrochloride, 2.70 g (10.3 mmol) of 4-amino-3-iodobenzoic acid, 1.39 g (10.3 mmol) of HOBt, 2.16 g (11.3 mmol) of EDC and 6.63 g (51.3 mmol) of N,N-diisopropylethylamine in 150 ml of DMF was stirred at room temperature for 16 h. 300 ml of water were added, and the aqueous phase was extracted three times with 300 ml of ethyl acetate each time. The combined organic phases were dried over sodium sulfate and the solvent was distilled off in vacuo. The residue was purified on a flash column (mobile phase: dichloromethane/methanol/triethylamine 90:10:0.2). 3.45 g (87%) of the desired title compound were obtined.

HPLC (conditions as in Example 1A): Rt=3.29 min $^1$H-NMR (200 MHz in $D_6$-DMSO) δ=1.18-1.87 (m, 5H), 2.58-3.13 (m, 6H), 3.49 (m, broad, 1H), 3.89 (m, 1H), 5.75 (m, 3H), 6.72 (d, 1H), 7.63 (dd, 1H), 7.92 (d, 1H), 8.12 (d, 1H)

MS (ESI+): m/z=372 $[M+H]^+$

EXAMPLE 3A

N-(1-Azabicyclo[2.2.2]oct-3-yl)-4-iodo-3-nitrobenzamide

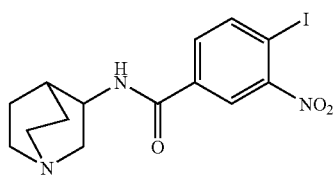

A solution of 3.08 g (24.4 mmol) of 3-aminoquinuclidine dihydrochloride, 7.60 g (24.4 mmol) of 4-iodo-3-nitrobenzoyl chloride, 9.88 g (97.6 mmol) of triethylamine in 150 ml of DMF was stirred at room temperature overnight. The solvent was distilled off in a rotary evaporator, the residue was taken up in 200 ml of dichloromethane, and 200 ml of a saturated sodium bicarbonate solution were added. The organic phase was dried over sodium sulfate, and the solvent was distilled off in vacuo. 2.20 g (22.5%) of the desired title compound were obtained.

HPLC (conditions as in Example 1A): Rt=3.72 min.

$^1$H-NMR (300 MHz in $CDCl_3$) δ=1.24-1.78 (m, 5H), 2.05 (m, 1H), 2.61 (m, 1H), 2.89 (m, 3H), 3.46 (m, 1H), 4.15 (m, 1H), 6.24 (m, 1H), 7.67 (dd, 1H), 8.14 (d, 1H), 8.20 (d, 1H).

MS (ESI+): m/z=402 $[M+H]^+$

EXAMPLE 4A

3-Amino-N-(1-azabicyclo[2.2.2]oct-3-yl)-4-iodobenzamide

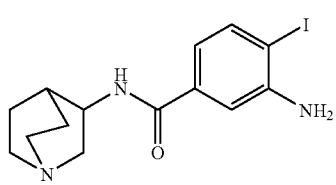

A solution of 100 mg (0.25 mmol) of N-(1-azabicyclo[2.2.2]oct-3-yl)-4-iodo-3-nitrobenzamide and 281 mg (1.25 mmol) of tin(II) chloride dihydrate in 5 ml of DMF was stirred at room temperature for 6 h. The solvent was distilled off in a rotary evaporator, the residue was taken up in 10 ml of dichloromethane, and 10 ml of aqueous 1 M sodium hydroxide solution were added. The organic phase was dried over sodium sulfate, and the solvent was distilled off in a rotary evaporator. 91 mg (98%) of the desired title compound were obtained.

HPLC (conditions as in Example 1A): Rt=3.28 min.

$^1$H-NMR (300 MHz in $D_6$-DMSO) δ=1.21-1.85 (m, 5H), 2.64 (m, 4H), 2.85 (m, 1H), 3.05 (m, 1H), 3.89 (m, 1H), 5.34 (s, broad, 2H), 6.78 (dd, 1H), 7.15 (m, 1H), 7.60 (d, 1H), 8.13 (d, 1H).

MS (ESI+): m/z=372 $[M+H]^+$

EXEMPLARY EMBODIMENTS

EXAMPLE 1

N-(1-Azabicyclo[2.2.2]oct-3-yl)-6-quinolinecarboxamide hydrochloride

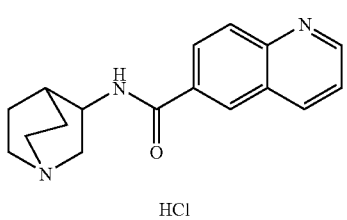

HCl

Firstly, 319 mg (0.99 mmol) of TBTU and 137 mg (1.01 mmol) of HOBt are added to a solution of 182 mg (1.05 mmol) of quinoline-6-carboxylic acid and diisopropylethylamine (620 mg, 4.8 mmol) in 4 mL of DMF at RT, and then 200 mg (1.0 mmol) of 3-aminoquinuclidine dihydrochloride are added. The mixture is stirred at RT for 4 h. For a workup, it is concentrated and taken up in a mixture of chloroform and excess aqueous NaOH. The phases are separated and the aqueous phase is back-extracted several times with chloroform. The combined organic phases are dried over sodium sulfate and concentrated, and the crude product is chromatographed on a silica gel column (mobile, chloroform:methanol: conc. $NH_3$=100:20:4). The resulting product is taken up in THF, excess HCl in diethyl ether is added, and the mixture is concentrated and dried under high vacuum. 136 mg (47% yield) of the hydrochloride are obtained.

$^1$H-NMR (300 MHz, $CD_3OD$) δ=9.30 (m, 2H); 8.95 (s, 1H); 8.60 (d, 1H), 8.32 (d, 1H); 8.15 (m, 1H); 4.55 (m, 1H), 3.85 (m, 1H); 3.60-3.30 (m, 5H); 2.50-1.90 (m, 5H).

MS (ESI+): m/z 282 ([M+H]$^+$ of the free base)

EXAMPLE 2

N-(1-Azabicyclo[2.2.2]oct-3-yl)-2-phenazinecarboxamide

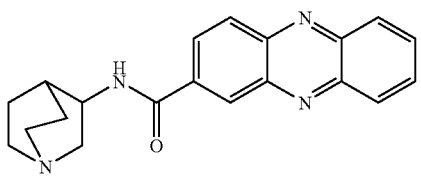

Prepared in analogy to the method for Example 1 starting from 236 mg of phenazine-2-carboxylic acid and 200 mg of 3-aminoquinuclidine dihydrochloride. 84 mg (25% yield) of the free base were obtained after chromatographic separation.

$^1$H-NMR (in DMSO-$d_6$) δ=8.85 (s, 1H); 8.75 (d, J=7 Hz, 1H); 8.30 (m, 4H); 8.00 (m, 2H); 4.05 (m, 1H); 3.2-2.7 (m, 6H); 2.0-1.3 (m, 5H).

MS (ESI+): m/z=333 [M+H]$^+$

EXAMPLE 3

N-(1-Azabicyclo[2.2.2]oct-3-yl)-7-quinolinecarboxamide hydrochloride

HCl

Prepared in analogy to the method for Example 1 starting from 183 mg of quinoline-7-carboxylic acid (Seibert et al. *J. Am. Chem. Soc.* 1946, 68, 2721) and 200 mg of 3-aminoquinuclidine dihydrochloride. 227 mg (71% yield) of the hydrochloride were obtained.

$^1$H-NMR (300 MHz in DMSO-$d_6$) δ=10.5 (s, 1H); 9.15 (m, 2H); 8.70 (m, 2H), 8.20 (m, 2H); 7.80 (m, 1H); 4.40 (m, 1H); 3.65 (m, 1H), 3.45-3.10 (m, 5H); 2.30-1.65 (m, 5H).

MS (ESI+): m/z=282 ([M+H]$^+$ of the free base)

EXAMPLE 4

N-[(3R)-1-Azabicyclo[2.2.2]oct-3-yl]-6-quinolinecarboxamide hydrochloride

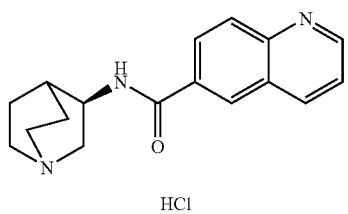

HCl

Prepared in analogy to Example 1 starting from (3R)-1-azabicyclo[2.2.2]oct-3-ylamine. The $^1$H-NMR and MS data were identical to Example 1.

EXAMPLE 5

N-(1-Azabicyclo[2.2.2]oct-3-yl)-2-ethyl-7-quinolinecarboxamide

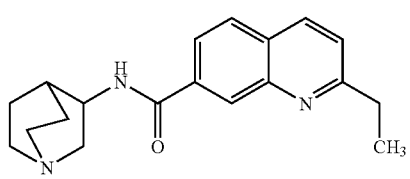

A solution of 30 mg (0.08 mmol) of Example 4A, 0.32 mmol of 1-penten-3-ol, 0.5 mg (10 mol %) of palladium(II) acetate, 22.4 mg (0.08 mmol) of tetrabutyl-ammonium chloride, 0.6 mg (10 mol %) of tri-tert-butylphosphine and 28 mg (0.20 mmol) of potassium carbonate in 2 ml of DMF was stirred at 100° C. in an argon atmosphere for 72 h. The solvent was distilled off and the residue was taken up in methanol. It was purified by thick-layer chromatography (mobile phase: dichloro-methane/methanol/triethylamine 80:20:2). The title compound was obtained in 12% yield.

HPLC (conditions as in Example 1A): Rt=3.00 min.

$^1$H-NMR (400 MHz in D$_6$-DMSO) δ=1.35 (t, 3H), 1.21-2.01 (m, 5H), 2.96 (q, 2H), 2.82-3.12 (m, 5H), 4.11 (m, 1H), 7.52 (d, 1H), 7.95 (m, 2H), 8.31 (d, 1H), 8.54 (s, 1H), 8.64 (d, 1H).

MS (ESI+): m/z=310 [M+H]$^+$

EXAMPLE 6

N-(1-Azabicyclo[2.2.2]oct-3-yl)-2-ethyl-6-quinolinecarboxamide

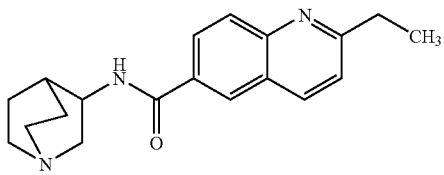

Example 2A was reacted with 1-penten-3-ol in analogy to the method for Example 5. The title compound was obtained in 36% yield.

LC/MS (Kromasil RP-18, 5 µm, 2.1×150 mm, eluent=A: acetonitrile B: H$_2$O+0.23 g 30% HCl/1 water; gradient=0-2.5 min 2% A—95% A; 2.5-5 min 95% A; flow rate=0.9 mL/min; temp.: 70° C., UV detection at 210 min): Rt=1.71 min; MS (ESI+): m/z=310 [M+H]$^+$.

$^1$H-NMR (400 MHz in D$_6$-DMSO) δ=1.32 (t, 3H), 1.25-2.22 (m, 5H), 2.76 (m, 4H), 2.97 (m, 5H), 4.06 (m, 1H), 7.52 (d, 1H), 7.98 (d, 1), 8.12 (dd, 1H), 8.36 (d, 1H), 8.43 (s, 1H), 8.52 (d, 1H).

EXAMPLE 7

N-(1-Azabicyclo[2.2.2]oct-3-yl)-2-methyl-7-quinolinecarboxamide

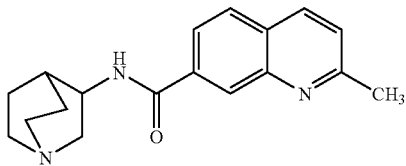

Example 4A was reacted with 1-buten-3-ol in analogy to the method for Example 5. The title compound was obtained in 21% yield.

LC/MS (conditions as in Example 6): Rt=1.70 min; MS (ESI+): m/z=296 [M+H]$^+$.

$^1$H-NMR (400 MHz in D$_6$-DMSO) δ=1.38-1.99 (m, 5H), 2.68 (s, 3H), 2.82 (m, 4H), 3.01 (m, 1H), 4.10 (m, 1H), 7.50 (d, 1H), 7.96 (m, 2H), 8.30 (d, 1H), 8.51 (s, 1H), 8.60 (s, 1H).

EXAMPLE 8

N-(1-Azabicyclo[2.2.2]oct-3-yl)-2-methyl-6-quinolinecarboxamide

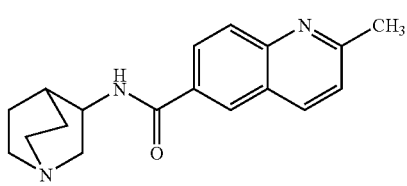

Example 2A was reacted with 1-buten-3-ol in analogy to the method for Example 5. The title compound was obtained in 29% yield.

LC/MS (conditions as in Example 6): Rt=0.57 min; MS (ESI+): m/z=296 [M+H]$^+$.

EXAMPLE 9

N-(1-Azabicyclo[2.2.2]oct-3-yl)-4-methyl-6 quinolinecarboxamide

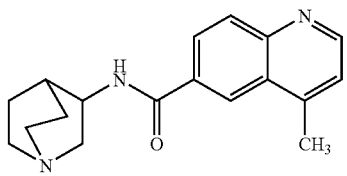

Example 2A was reacted with 2-butyn-1-ol in analogy to the method for Example 5. The title compound was obtained in 8% yield.

LC/MS (conditions as in Example 6): Rt=0.56 min; MS (ESI+): m/z=296 [M+H]$^+$.

EXAMPLE 10

N-(1-Azabicyclo[2.2.2]oct-3-yl)-2-propyl-6-quinolinecarboxamide

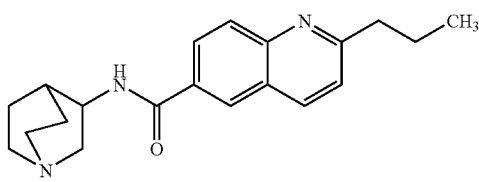

Example 2A was reacted with 1-hexen-3-ol in analogy to the method for Example 5. The title compound was obtained in 23% yield.

LC/MS (conditions as in Example 6): Rt=1.77 min; MS (ESI+): m/z=324 [M+H]$^+$.

$^1$H-NMR (400 MHz in D$_6$-DMSO) δ=0.95 (t, 3H), 1.24-1.65 (m, 4H), 1.85 (m, 4H), 2.70 (m, 3H), 2.91 (m, 3H), 3.15 (m, 1H), 4.01 (m, 1H), 5.76 (m, 1H), 7.50 (d, 1H), 7.96 (m, 1H), 8.12 (d, 1H), 8.38 (d, 1H), 8.47 (m, 2H).

EXAMPLE 11

N-(1-Azabicyclo[2.2.2]oct-3-yl)-2-ethyl-4-methyl-6-quinolinecarboxamide

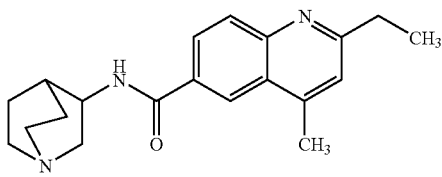

Example 2A was reacted with 2-hexyn-4-ol in analogy to the method for Example 5. The title compound was obtained in 16% yield.

LC/MS (conditions as in Example 6): Rt=2.06 min; MS (ESI+): m/z=324 [M+H]$^+$.

$^1$H-NMR (400 MHz in D$_6$-DMSO) δ=1.31 (t, 3H), 1.61 (m, 2H), 1.90 (m, 2H), 2.71 (m, 8H), 2.91 (m, 4H), 3.17 (m, 1H), 4.01 (m, 1H), 7.39 (s, 1H), 7.95 (d, 1H), 8.13 (m, 1H), 8.49 (m, 2H).

EXAMPLE 12

N-(1-Azabicyclo[2.2.2]oct-3-yl)-2-propyl-7-quinolinecarboxamide

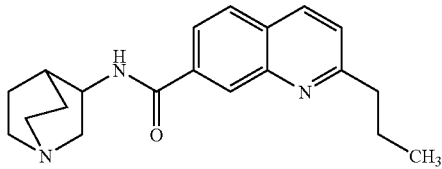

Example 4A was reacted with 1-hexen-3-ol in analogy to the method for Example 5. The title compound was obtained in 12% yield.

LC/MS (conditions as in Example 6): Rt=1.73 min; MS (ESI+): m/z=324 [M+H]$^+$.

$^1$H-NMR (400 MHz in D$_6$-DMSO) δ=0.96 (t, 3H), 1.38 (m, 1H), 1.63 (m, 2H), 1.87 (m, 5H), 2.75 (m, 5H), 2.93 (m, 3H), 3.20 (m, 1H), 4.05 (m, 1H), 7.50 (d, 1H), 7.96 (m, 2H), 8.30 (m, 1H), 8.54 (s, 1H), 8.61 (d, 1H).

EXAMPLE 13

N-(1-Azabicyclo[2.2.2]oct-3-yl)-2-ethyl-4-methyl-7-quinolinecarboxamide

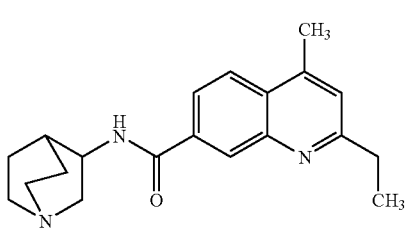

Example 4A was reacted with 2-hexyn-4-ol in analogy to the method for Example 5. The title compound was obtained in 15% yield.

LC/MS (conditions as in Example 6): Rt=1.73 min; MS (ESI+): m/z=324 [M+H]$^+$.

$^1$H-NMR (400 MHz in D$_6$-DMSO) δ=1.32 (t, 3H), 1.60 (m, 2H), 1.85 (m, 1H), 2.70 (m, 8H), 2.92 (m, 4H), 3.12 (m, 1H), 4.02 (m, 1H), 7.40 (s, 1H), 7.97 (d, 1H), 8.10 (d, 1H), 8.53 (m, 1H), 8.59 (d, 1H).

EXAMPLE 14

N-(1-Azabicyclo[2.2.2]oct-3-yl)-4-(tetrahydro-2H-pyran-2-yl)-6-quinoline-carboxamide

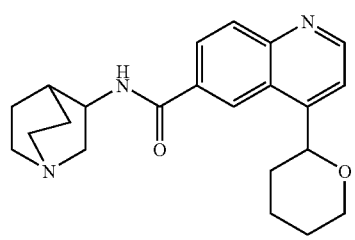

Example 2A was reacted with 3-(tetrahydro-2H-pyran-2-yl)-2-propyn-1-ol in analogy to the method for Example 5. The title compound was obtained in 12% yield.

LC/MS (conditions as in Example 6): Rt=1.78 min; MS (ESI+): m/z=366 [M+H]$^+$.

$^1$H-NMR (400 MHz in D$_6$-DMSO) δ 1.22-2.05 (m, 13H), 2.71 (m, 5H), 2.90 (m, 2H), 3.17 (m, 1H), 3.76 (m, 1H), 4.00 (m, 1H), 4.16 (m, 1H), 5.18 (d, 1H), 7.60 (d, 1H), 8.05 (d, 1H), 8.18 (d, 1H), 8.52 (s, 1H), 8.94 (d, 1H).

EXAMPLE 15

N-(1-Azabicyclo[2.2.2]oct-3-yl)-4-(tetrahydro-2H-pyran-2-yl)-7-quinoline-carboxamide

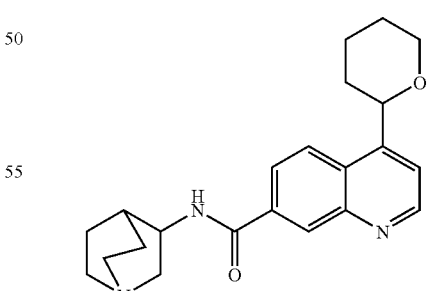

Example 4A was reacted with 3-(tetrahydro-2H-pyran-2-yl)-2-propyn-1-ol in analogy to the method for Example 5. The title compound was obtained in 9% yield.

LC/MS (conditions as in Example 6): Rt=1.92 min; MS (ESI+): m/z=366 [M+H]$^+$.

EXAMPLE 16

N-(1-Azabicyclo[2.2.2]oct-3-yl)-2-phenyl-6-quinolinecarboxamide

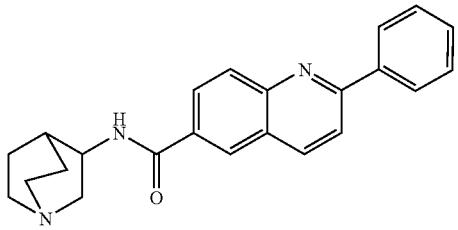

Intermediate 2 was reacted with 3-phenyl-1-propen-3-ol in accordance with the general method. The title compound was obtained in 38% yield.

LC/MS (conditions as in Example 6): Rt=1.94 min; MS (ESI+): m/z=358 [M+H]$^+$.

EXAMPLE 17

N-(1-Azabicyclo[2.2.2]oct-3-yl)-2-phenyl-7-quinolinecarboxamide

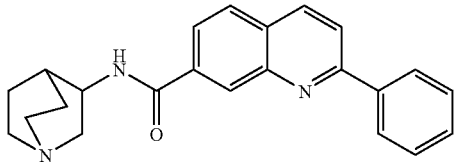

Example 4A was reacted with 3-phenyl-1-propen-3-ol in analogy to the method for Example 5. The title compound was obtained in 24% yield.

LC/MS (conditions as in Example 6): Rt=1.95 min; MS (ESI+): m/z=358 [M+H]$^+$.

The invention claimed is:

1. A compound of the formula (I)

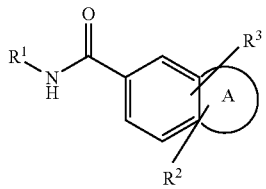

in which
R$^1$ is an azabicyclo[m.n.o]alkyl radical having 7 to 11 ring atoms, in which m, n and o are identical or different and are 0, 1, 2 or 3,
and where the radical is optionally substituted by (C$_1$-C$_6$)-alkyl,
the ring A is pyrimido, or
is optionally benzo-fused pyrido, pyridazo or pyridazino, and
R$^2$ and R$^3$ are identical or different and are radicals selected from the group of hydrogen, halogen, formyl, carbamoyl, cyano, trifluoromethyl, trifluoromethoxy, nitro, (C$_1$-C$_6$)-alkyl, (C$_1$-C$_6$)-alkoxy, (C$_1$-C$_6$)-alkylthio, (C$_3$-C$_8$)-cycloalkyl, 4- to 8-membered heterocyclyl, phenyl or 5- to 6-membered heteroaryl, where phenyl and heteroaryl are optionally substituted by halogen, (C$_1$-C$_4$)-alkyl, (C$_1$-C$_4$)-alkoxy, amino, mono- or di-(C$_1$-C$_4$)-alkylamino, (C$_1$-C$_4$)-alkanoylamino or (C$_1$-C$_4$)-alkanesulfonylamino,
or a salt thereof.

2. A compound as claimed in claim 1, where
R$^1$ has the meaning indicated in claim 1,
the ring A together with the fused-on benzene residue is quinolin-5-yl or quinolin-6-yl,
and
R$^2$ and R$^3$ are identical or different and are radicals selected from the group of hydrogen, halogen, cyano, trifluoromethyl, methyl and ethyl,
or a salt thereof.

3. A compound as claimed in claim 1 or 2, where
R$^1$ is 1-azabicyclo[2.2.2]oct-3-yl,
and ring A, R$^2$ and R$^3$ have the meaning indicated in claim 1 or 2,
or a salt thereof.

4. A process for preparing compounds of the formula (I) as claimed in claim 1, characterized in that compounds of the general formula (II)

$$R_1-NH_2 \qquad (II)$$

in which R$^1$ has the meaning indicated in claim 1,
are reacted with a compound of the general formula (III)

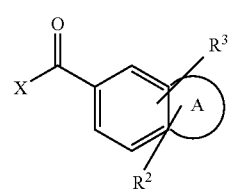

in which
the ring A, R$^2$ and R$^3$ have the meaning indicated in claim 1, and
X is hydroxyl or a suitable leaving group,
in an inert solvent, where appropriate in the presence of a condensing agent, and where appropriate in the presence of a base.

5. A pharmaceutical composition comprising at least one compound as claimed in any of claims 1 to 3 in combination with at least one pharmaceutically acceptable, essentially nontoxic carrier or excipient.

* * * * *